(12) United States Patent
von Luehmann et al.

(10) Patent No.: US 10,799,161 B2
(45) Date of Patent: Oct. 13, 2020

(54) BIOSIGNAL ACQUISITION DEVICE AND SYSTEM, METHOD FOR ACQUISITION OF BIOSIGNALS

(71) Applicant: Technische Universität Berlin, Berlin (DE)

(72) Inventors: Alexander von Luehmann, Berlin (DE); Klaus-Robert Mueller, Berlin (DE)

(73) Assignee: Technische Universität Berlin, Berlin (DE)

( * ) Notice: Subject to any disclaimer, the term of this patent is extended or adjusted under 35 U.S.C. 154(b) by 583 days.

(21) Appl. No.: 15/090,141

(22) Filed: Apr. 4, 2016

(65) Prior Publication Data

US 2017/0281014 A1  Oct. 5, 2017

(51) Int. Cl.
*A61B 5/1455* (2006.01)
*A61B 5/00* (2006.01)
(Continued)

(52) U.S. Cl.
CPC ........ *A61B 5/14551* (2013.01); *A61B 5/0086* (2013.01); *A61B 5/0476* (2013.01); *A61B 5/0478* (2013.01); *A61B 5/4064* (2013.01); *A61B 5/6814* (2013.01); *A61B 5/7203* (2013.01); *A61B 5/7225* (2013.01); *H04L 27/0002* (2013.01); *A61B 5/0006* (2013.01);
(Continued)

(58) Field of Classification Search
CPC .................. G02B 6/43; H04L 27/0002; A61B 2562/0219; A61B 2562/0233; A61B 2562/06; A61B 5/14551; A61B 5/0086; A61B 5/0476; A61B 5/0478; A61B 5/4064; A61B 5/6814; A61B 5/7203; A61B 5/7225; A61B 5/0006; A61B 5/0075; A61B 5/04012; A61B 5/04085; A61B 5/0492; A61B 5/0496; A61B 5/721; G06F 3/015
See application file for complete search history.

(56) References Cited

U.S. PATENT DOCUMENTS 6,424,320 B1 *  7/2002  Callway ................ G06F 3/1438
                                                        345/1.1
8,396,525 B2    3/2013  Ishikawa et al.
(Continued)

FOREIGN PATENT DOCUMENTS

| CN | 202161317 U   | 3/2012  |
|----|---------------|---------|
| CN | 104146707 A   | 11/2014 |
| JP | 2003322612 A  | 11/2003 |

OTHER PUBLICATIONS

Allison et al., "Toward smarter BCIs: extending BCIs through hybridization and intelligent control," Journal of Neural Engineering, 2012, pp. 1-7, vol. 9, No. 1.
(Continued)

*Primary Examiner* — Stephen G Sherman
(74) *Attorney, Agent, or Firm* — The Webb Law Firm

(57) ABSTRACT

Disclosed is a biosignal acquisition device for the acquisition, in particular the concurrent or simultaneous acquisition, of optical and electrical biosignals. The optical and electrical biosignals are both received by an analog front end device for biosignals, with an opto-electric converter for converting the optical biosignals into electrical signals. Also disclosed are a system of a plurality of biosignal acquisition devices and a biosignal acquisition method.

18 Claims, 14 Drawing Sheets

(51) Int. Cl.
    *H04L 27/00* (2006.01)
    *A61B 5/0478* (2006.01)
    *A61B 5/0476* (2006.01)
    *A61B 5/0496* (2006.01)
    *A61B 5/0492* (2006.01)
    *A61B 5/04* (2006.01)
    *A61B 5/0408* (2006.01)

(52) U.S. Cl.
    CPC ......... *A61B 5/0075* (2013.01); *A61B 5/04012* (2013.01); *A61B 5/04085* (2013.01); *A61B 5/0492* (2013.01); *A61B 5/0496* (2013.01); *A61B 5/721* (2013.01); *A61B 2562/0219* (2013.01); *A61B 2562/0233* (2013.01); *A61B 2562/06* (2013.01)

(56) References Cited

U.S. PATENT DOCUMENTS

| | | | |
|---|---|---|---|
| 2007/0083097 | A1 | 4/2007 | Fujiwara et al. |
| 2009/0292658 | A1* | 11/2009 | Jung ................. G06N 5/04 706/11 |
| 2010/0240971 | A1 | 9/2010 | Zanatta |
| 2011/0054583 | A1* | 3/2011 | Litt ................. A61B 5/0031 607/116 |
| 2011/0112382 | A1* | 5/2011 | Li ................. A61B 5/02427 600/301 |
| 2013/0274712 | A1* | 10/2013 | Schecter ............ A61M 25/10 604/510 |
| 2015/0084860 | A1* | 3/2015 | Aleem .................. G06F 3/017 345/156 |
| 2015/0169074 | A1* | 6/2015 | Ataee .................. G06F 3/017 345/156 |
| 2016/0116516 | A1* | 4/2016 | Xia ..................... G01R 27/28 324/609 |
| 2017/0172447 | A1* | 6/2017 | Mitra .................. A61B 5/0075 |
| 2017/0224246 | A1 | 8/2017 | Jiang et al. |

OTHER PUBLICATIONS

Andreu-Perez et al., "From Wearable Sensors to Smart Implants—Toward Pervasive and Personalized Healthcare," IEEE Transactions on Biomedical Engineering, 2015, pp. 2750-2762, vol. 62, No. 12.

Atsumori et al., "Development of a Multi-Channel, Portable Optical Topography System," Engineering in Medicine and Biology Society, 2007, pp. 3362-3364.

Ayaz et al., "Continuous monitoring of brain dynamics with functional near infrared spectroscopy as a tool for neuroergonomic research: empirical examples and a technological development," Frontiers in Human Neuroscience, Dec. 2013, pp. 1-13, vol. 7, No. 871.

Biessmann et al., "Temporal kernel CCA and its application in multimodal neuronal data analysis," Machine Learning, 2010, pp. 5-27, vol. 79.

Blankertz et al., "The Berlin brain-computer interface: non-medical uses of BCI technology," Frontiers in Neuroscience, Dec. 2010, pp. 1-17, vol. 4, No. 198.

Calhoun et al., "A review of group ICA for fMRI data and ICA for joint inference of imaging, genetic, and ERP data," NeuroImage, 2009, p. S163-S172, vol. 45.

Daehne et al., "Integration of multivariate data streams with bandpower signals," IEEE Transactions on Multimedia, 2013, pp. 1001-1013, vol. 15, No. 5.

Daehne et al., "Multivariate machine learning methods for fusing multimodal functional neuroimaging data," Proceedings of the IEEE, 2015, pp. 1-24, vol. 103, No. 9.

Debener et al., "How about taking a low-cost, small, and wireless EEG for a walk?", Psychophysiology, 2012, pp. 1449-1453, vol. 49.

Debener et al., "Unobtrusive ambulatory EEG using a smartphone and flexible printed electrodes around the ear," Scientific Reports, 2015, pp. 1-11, vol. 5, No. 16743.

Fazli et al., "Enhanced performance by a hybrid NIRS-EEG brain computer interface," NeuroImage, 2012, pp. 519-529, vol. 59.

Fazli et al., "Learning From More Than One Data Source: Data Fusion Techniques for Sensorimotor Rhythm-Based Brain-Computer Interfaces," Proceedings of the IEEE, Jun. 2015, pp. 891-906, vol. 103, No. 6.

Huppert et al., "HomER: a review of time-series analysis methods for near-infrared spectroscopy on the brain," Applied Optics, 2009, Abstract of pp. D280-D298, vol. 48, No. 10.

Lareau et al., "Near Infrared Spectrometer Combined with Multi-channel EEG for Functional Brain Imaging," Medical Information Communication Technology 5th International Symposium, 2011, pp. 122-126.

Looney et al., "An In-The-Ear Platform for Recording Electroencephalogram," 33rd Annual International Conference of the IEEE Engineering in Medicine and Biology Society, Aug. 2011, pp. 6882-6885.

"Low-Noise, 8-Channel, 24-Bit Analog Front-End for Biopotential Measurements," Datasheet: ADS1299, Aug. 2012, Texas Instruments.

Mueller et al., "Machine learning for real-time single-trial EEG-analysis: From brain-computer interfacing to mental state monitoring," Journal of Neuroscience Methods, 2008, pp. 82-90, vol. 167.

Mueller-Putz et al., "Towards Noninvasive Hybrid Brain-Computer Interfaces: Framework, Practice, Clinical Application, and Beyond," Proceedings of the IEEE, 2015, pp. 926-943, vol. 103, No. 6.

"OPT101: Monolithic Photodiode and single-supply transimpedance amplifier," Mar. 1998, pp. 1-11, Burr-Brown.

Parasuraman, "Neuroergonomics: Brain, Cognition, and Performance at Work," Current Directions in Psychological Science, 2011, pp. 181-186, vol. 20, No. 3.

Parasuraman, "Neuroergonomics: Research and practice," Theoretical Issues in Ergonomics Science, 2003, pp. 5-20, vol. 4, Nos. 1-2, 5-20.

Pfurtscheller et al., "The hybrid BCI," Frontiers in Neuroscience, Apr. 21, 2010, pp. 1-11, vol. 4, No. 3.

Picton et al., "Human Auditory Evoked Potentials I: Evaluation of Components," Electroencephalography and Clinical Neurophysiology, Mar. 1974, pp. 179-190, vol. 36.

Safaie et al., "Toward a fully integrated wireless wearable EEG-NIRS bimodal acquisition system," Journal of Neural Engineering, 2013, pp. 1-11, vol. 10, No. 5.

Scholkmann et al., "A review on continuous wave functional near-infrared spectroscopy and imaging instrumentation and methodology," NeuroImage, 2013, pp. 1-22, vol. 85.

Swartling et al., "Comparison of spatially and temporally resolved diffuse-reflectance measurement systems for determination of biomedical optical properties," Applied Optics, 2003, Abstract of pp. 4612-4620, vol. 42, No. 22.

Von Luehmann et al., "Toward a Wireless Open Source Instrument: Functional Near-infrared Spectroscopy in Mobile Neuroergonomics and BCI Applications," Frontiers in Human Neuroscience, Nov. 12, 2015, pp. 1-14, vol. 9, No. 617.

Wabnitz et al., "Performance assessment of time-domain optical brain imagers, part 1: basic instrumental performance protocol," Journal of Biomedical Optics, 2014, pp. 1-12, vol. 19, No. 8.

Wabnitz et al., Characterization of homogeneous tissue phantoms for performance tests in diffuse optics, Proceedings of SPIE, 2016, pp. 1-7.

Zander et al., "Towards passive brain-computer interfaces: applying brain-computer interface technology to human-machine systems in general," Journal of Neural Engineering, 2011, pp. 1-5, vol. 8.

Zhang et al., "Experimental Comparison of Using Continuous-Wave and Frequency-Domain Diffuse Optical Imaging Systems to Detect Heterogeneities," Proceedings of SPIE, 2001, pp. 219-231, vol. 4250.

Zheng et al., "Unobtrusive Sensing and Wearable Devices for Health Informatics," IEEE Transactions on Biomedical Engineering, May 2014, pp. 1538-1554, vol. 61, No. 5.

Jindal et al., "Development of Point of Care Testing Device for Neurovascular Coupling From Simultaneous Recording of EEG and

(56) References Cited

OTHER PUBLICATIONS

NIRS During Anodal Transcranial Direct Current Stimulation", IEEE Journal of Translational Engineering in Health and Medicine, 2015, 12 Pages, vol. 3.

Zhang et al., "Development of motion resistant instrumentation for ambulatory near-infrared spectroscopy", Journal of Biomedical Optics, Aug. 2011, 14 Pages, vol. 16(8).

* cited by examiner

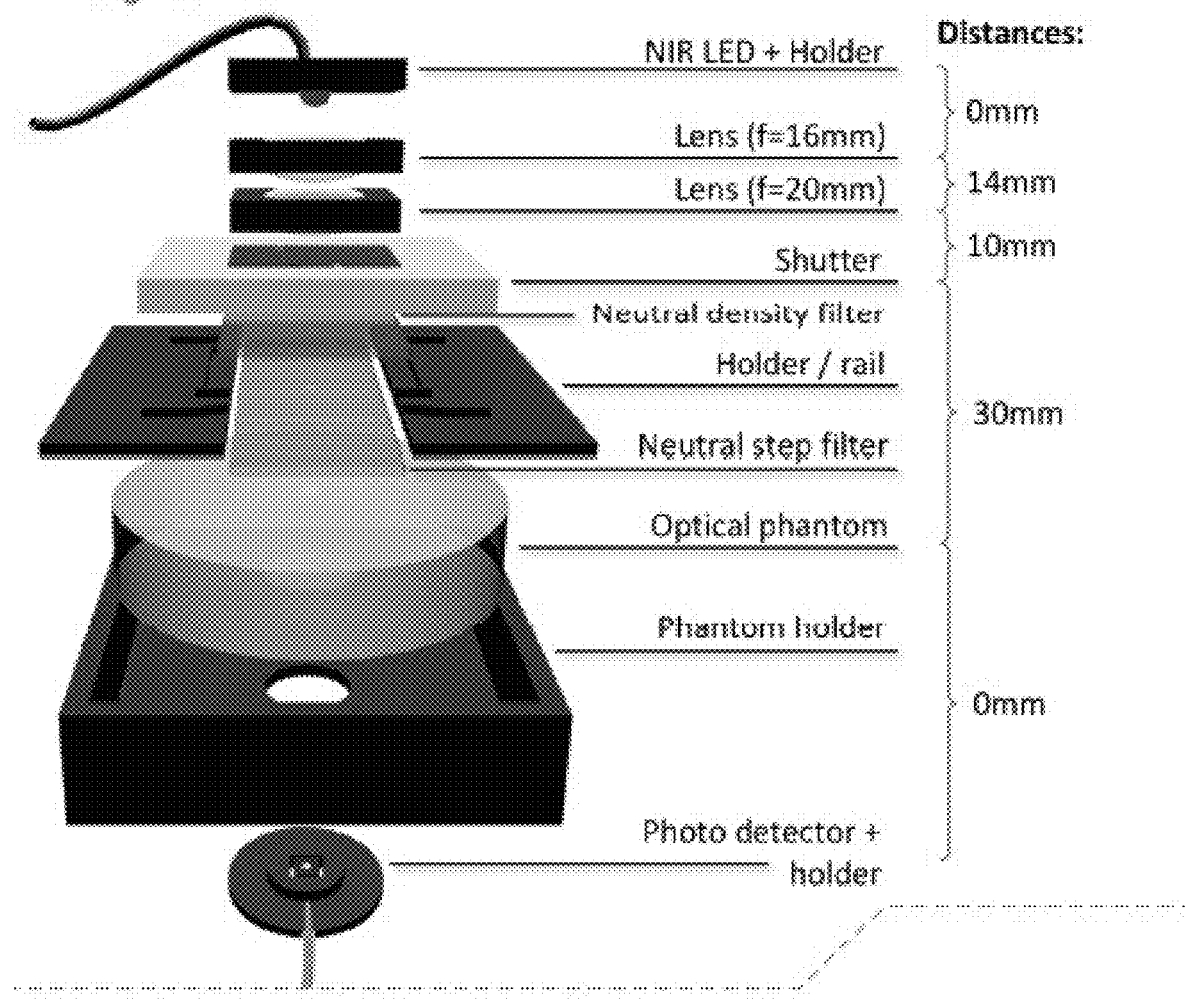

US 10,799,161 B2

BIOSIGNAL ACQUISITION DEVICE AND SYSTEM, METHOD FOR ACQUISITION OF BIOSIGNALS

BACKGROUND OF THE INVENTION

Field of the Invention

The invention relates to a biosignal acquisition device, a system of biosignal acquisition devices, and a method for the acquisition of biosignals for use particularly in the fields of telemedicine, neurotechnology and Brain-Computer Interfaces (BCI), hybrid multimodal acquisition technology and signal processing gain momentum. Therefore, efficient devices, systems and methods for the mobile acquisition of biosignals are required.

Description of Related Art

Initiated by wearable computers and smartphones with increasing computational capacity, a trend towards mobile body sensors, telemedicine and pervasive healthcare is ongoing. While acquisition hardware and sensors become more and more miniaturized, communication technology also rapidly changes towards extremely low latencies in combination with high availability, reliability and security (e.g. tactile internet). As a result, wireless body sensor networks (WBSNs) become possible that use and fuse an increasing number of bio-signal modalities and integrate contextual environmental information.

In another domain, the domain of Brain-Computer Interfaces (BCI), the range of—mainly static—applications has substantially been enlarged by combining BCI with other physiological or technical signals over the last decade.

Also, functional Near-Infrared Spectroscopy (fNIRS) joined the modality set used for multi-modal BCI or for the enhancement of Electroencephalogram (EEG) based BCI. fNIRS is a noninvasive optical technology for the local measurement of oxy- (O2HB) and deoxy-(HHB) hemoglobin concentration changes in cortical brain areas that use at least two wavelengths in the near-infrared spectrum of light. These so called "hybrid BCI"s (see G. Pfurtscheller, et al., "The hybrid BCI," Frontiers in Neuroscience, vol. 4, no. 3, 2010) show the potential to significantly increase the amount of information by using both common and complementary information in the set of signals. This also increases the options for approaches to enable more robust operation under harsher conditions in real-life scenarios.

These advancements also influence new research areas that are linked to both domains: Neuroergonomics and adaptive neurotechnology research focus on the use of brain and body biosignals for the design of new technologies that—in a more general human-machine interface sense—improve work environments, efficiency and security and advance the understanding of brain function in real-world scenarios.

SUMMARY OF THE INVENTION

The embodiments described here contribute to the advancing of e.g. BCI technology further towards applications out of the lab and into a broader context of wearable sensor applications that go beyond traditional BCIs by the use of hybridization and contextualization.

The embodiments described herein comprises an architecture for a new generation of mobile miniaturized hybrid bio-optical and bio-electrical designs that are generally compatible with WBSN scenarios.

While the general approach works for a variety of applications and signals, most embodiments described herein are used in hybrid neurotechnology solutions, especially BCI and neuroergonomics, by focusing on fNIRS and EEG bio signals as main modalities and accelerometer, electrocardiogram (ECG) and electromyogram (EMG) as additional modalities.

Functional modules from the open source fNIRS design can be used to cost-effectively create hybrid bio-signal acquisition technology that measures both electrical and optical signals.

Known fNIRS solutions are generally backpack-sized and are not miniaturized enough to be worn directly on the body or are limited to application on the forehead.

Besides the aim to implement a design that considers the above issues, three additional goals can be set for embodiments of the novel architecture for biosignal acquisition devices, systems and methods:

- For a flexible WBSN scenario, modules can be modularly combined and are thus scalable but still independent.
- Additionally, at least two different bioelectrical modalities (usually with different references) should be measurable at the same time by a single module—for instance a low channel count EEG combined with a simultaneous ECG. This necessitated a design for a flexible setup of the bio-potential references.
- At last, a comparatively cheap, known integrated circuits can be used to ensure long term availability on the market and availability of detailed performance characteristics.

BRIEF DESCRIPTION OF THE DRAWINGS

The invention is described in the following in an exemplary way making reference to drawings.

FIG. 4A shows an experimental setup for optical NIRS characterization;

DETAILED DESCRIPTION OF THE INVENTION

In the following section, the instrumentation concept and system hardware architecture will be demonstrated. Then the devices, systems and methods used for the acquisition of physiological data in user studies, optical and electrical characteristics and some qualitative results of acquired physiological data are described. Finally, the results are discussed.

Instrumentation

Figure 1:
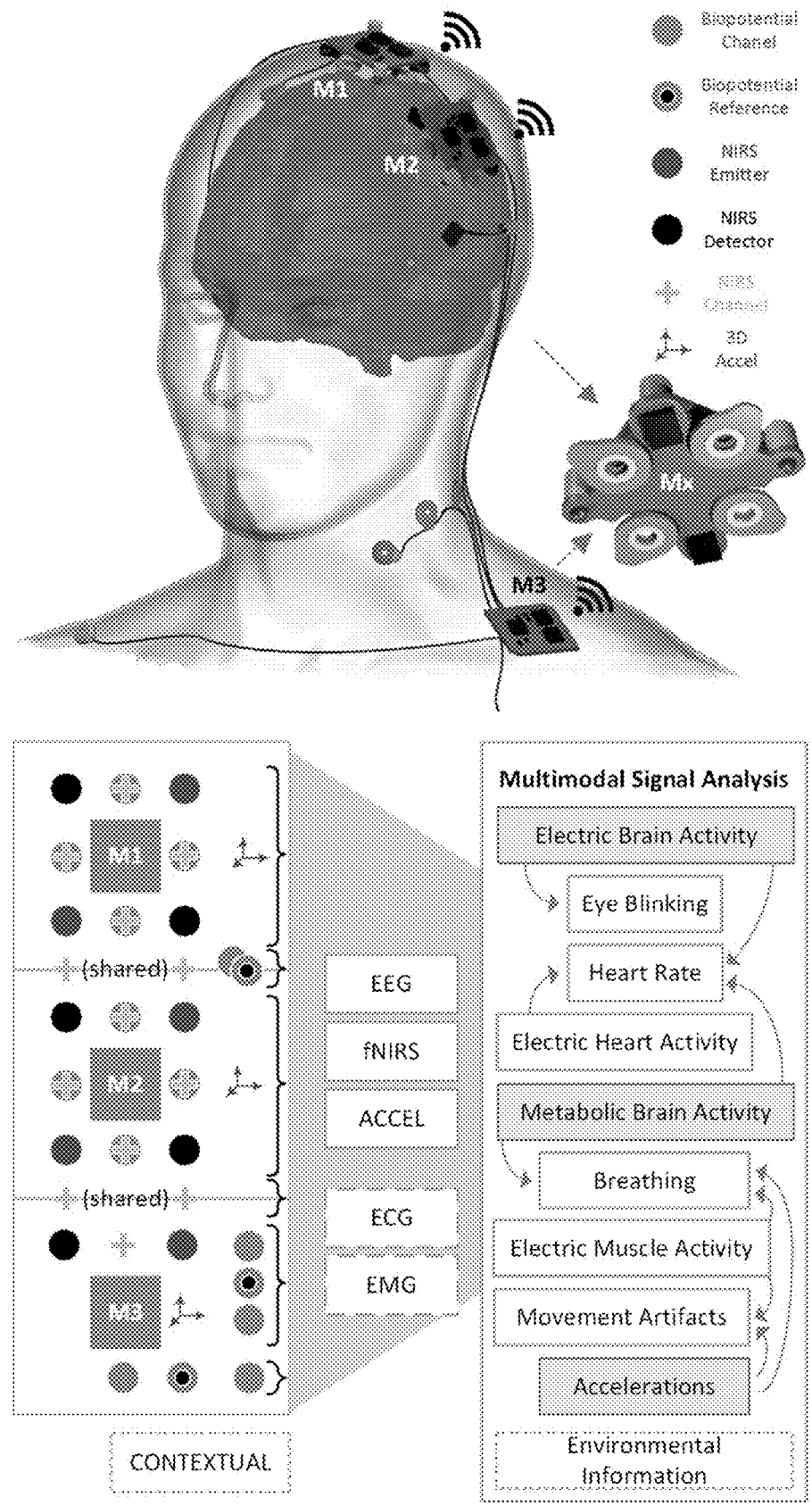
FIG. 1 shows a multimodal modular concept and example scenario for an embodiment of a system of biosignal acquisition devices.

Concept: To illustrate an embodiment of the device with the system concept and application goals for the Mobile, Modular, Multimodal Biosignal Acquisition (M3BA) device, FIG. 1 shows a typical hybrid WBSN BCI application scenario. Such a M3BA comprises an embodiment of a biosignal acquisition device.

Modules ($M_{x=1\ldots3}$) can be combined to increase fNIRS channel count and number of modalities acquired synchronously. The modules M1, M2, M3 form together a system comprising a number of biosignal acquisition devices which in particular can have an identical design.

Each module M1, M2, M3 provides 4+2 bio-electrical and 4+2 bio-optical signal acquisition channels and one 3D accelerometer. Multimodal signal analysis allows extraction of common and complementary information in the set.

While the detailed scenario and corresponding BCI studies are not in the scope of this disclosure, they exemplify a typical use case for which the modules were designed—including necessary characteristics such as modularity, mobility, miniaturization and multimodality, scalability and reconfigurable references. Also, they imply the resulting potential for multimodal signal analysis approaches:

A single M3BA module M1, M2, M3 provides 4+2 channels for bio-electrical signal acquisition, that are designed for scientific grade acquisition of EEG signals and can also be used for ECG, EMG and EOG (electrooculogram) recordings. Four channels derive signals against a fixed common reference. The additional two channels can be used for derivation against the same common electrode or (via microswitch) against another independent reference.

Each module M1, M2, M3 also provides 4+2 optical fNIRS channels (two detectors and emitters each), where the +2 channels are available when neighboring M3BA modules M1, M2, M3 share emitter/detector resources in a time division multiple access manner.

Additionally, each module M1, M2, M3 comprises a 3D-accelerometer for acquisition of acceleration data. Electrodes and optodes can but do not have to be fixed to the module M1, M2, M3. Thus, the module M1, M2, M3 can but does not have to be worn "on site", depending on the application, headgear or caps could be used.

In the example scenario in FIG. 1 (see upper part) three modules M1, M3, M3 are combined for simultaneous measurement of EEG, fNIRS, EMG and ECG: M1 and M2 and one optode pair of M3 measure 8 EEG and 13 fNIRS channels over the left somatosenory cortex, while M3 measures 2 EMG channels at the neck and 2 ECG channels on the chest.

M1 and M2 share a reference and ground electrode and make no use of the 4 EEG channels that are additionally available.

M3 uses the available reference split for the independent acquisition of EMG and ECG.

M1, M2 and M3 share fNIRS detector/emitter resources and thus create 4 shared fNIRS channels.

Where necessary, the modules M1, M2, M3 share a physical (non-wireless) interface for common time-critical signals such as a shared sampling clock and fNIRS channel control signals and—as in the case of M1 and M2—a common reference. All modules acquire movements (speed changes) via their 3D accelerometer.

The resulting set of synchronously acquired (bio-)signals enables a variety of new approaches for multimodal signal analysis. There has been an increasing number of novel methods that try to relate and optimize the amount of extracted information from the set that is common or complementary in the single modalities (such as kernel Cross Corellation Analysis (kCCA) and multimodal Source Power Correlation (mSPoC) (see Biesmann et al. "Temporal kernel CCA and its application in multimodal neuronal data analysis", Machine Learning, 2010, vol. 79, no. 1-2, pages 5-27; Daehne et al., "Multivariate Machine Learning Methods for Fusing Functional Multimodal Neuroimaging Data", Proceedings of the IEEE, 2015, volume 103, no. 9, pages 1507-1530; Daehne et al., "Integration of Multivariate Data Streams With Bandpower Signals, Multimedia, IEEE Transactions on Multimedia, 2013, volume 15, no. 5, pages 1001-1013).

Since the idea of multimodality is inherent to the system concept, some potential benefits in a non-conservative BCI perspective (using the brain signals as one but not the only input) are mentioned: In single modality analysis, (physiological or environmental) artifacts are usually to be suppressed maximally. When several modalities are combined in the analysis procedure, physiological and movement induced artifacts can be identified, suppressed or extracted more easily.

When extracted, they can even be used as additional parameters (such as heart rate, eye blinking frequency, etc.) for user state estimation in neuroergonomics or passive BCI scenarios. Typical examples for this are 1) the time-locked artifacts from heart activity as ECG in the EEG and pulse-waves in fNIRS recordings and 2) respiratory or movement related artifacts in EEG (EMG interference or electrode shifts) and fNIRS (modulation of oxy-/deoxy hemoglobin signals and optodeshifts) that are locked to synchronously acquired accelerometer data.

System hardware architecture: The hardware architecture (see FIG. 2, 9) was designed to concord with the system concept and to provide scientific grade system performance, precision and user safety.

Figure 9:
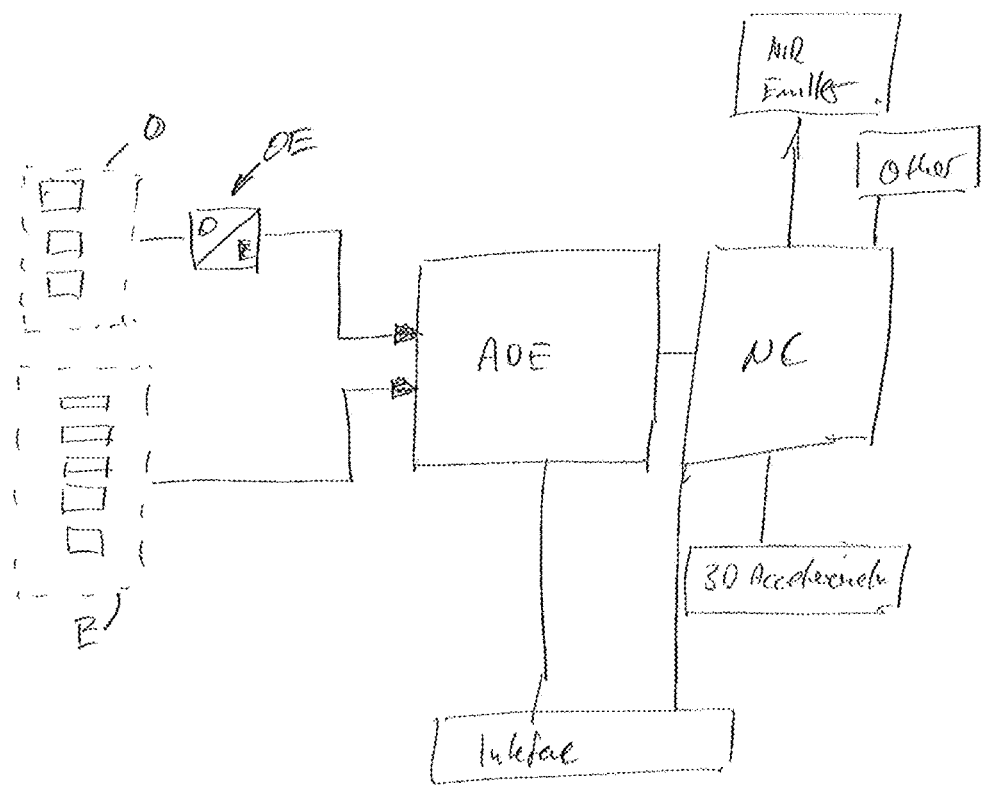
FIG. 9 shows a schematic overview comprising an embodiment of the biosignal acquisition device.

In FIG. 9 an overview of a first embodiment of a device for acquisition of optical and electrical biosignals is given, i.e. the device is designed to receive optical as well as electrical biosignals. The acquisition of the optical and electrical biosignals can be made in particular concurrently or simultaneously.

In FIG. 9 optical sensors O and electrical sensors E are schematically shown. Those sensors E, O are acquiring the biosignals as indicated in FIG. 1. The optical signals are converted into electrical signals by an opto-electronic converter OE. In one embodiment a monolithic photodiode and a single-supply transimpedance amplifier (Burr-Brown OPT101) is used as opto-electronic converter. The OPT101 is a monolithic photodiode with on-chip transimpedance amplifier. Output voltage increases linearly with light intensity. The amplifier is designed for single or dual power supply operation, making it ideal for battery operated equipment. The integrated combination of photodiode and transimpedance amplifier on a single chip eliminates the problems commonly encountered in discrete designs such as leakage current errors, noise pick-up and gain peaking due to stray capacitance. The 0.09×0.09 inch photodiode is operated in the photoconductive mode for excellent linearity and low dark current. The OPT101 operates from +2.7V to +36V supplies and quiescent current is only 120 mA. It is available in clear plastic 8-pin DIP, 5-pin SIP and J-formed DIP for surface mounting. Temperature range is 0° C. to 70° C.

In other embodiments, different photodiodes can be used in connection with the opto-electronic converter.

Therefore, the AFE only has to deal with electric signals so that not two separated units are required. The AFE can provide a parallel preprocessing and acquisition of differential biosignals.

The AFE is further connected to a microcontroller (μC) which drives among other things a NIR emitter circuit. Since the optical sensors and the optical emitters are both coupled via the AFE and the μC a closed loop system is realized. The emitter circuits can be controlled in dependence of the detected biosignals.

Therefore, the incoming biosignal data is jointly processed by the AFE and then transmitted to the microcontroller (μC). This allows an efficient synchronization of outgoing signals, i.e. no additional clocking device is required.

Figure 2:
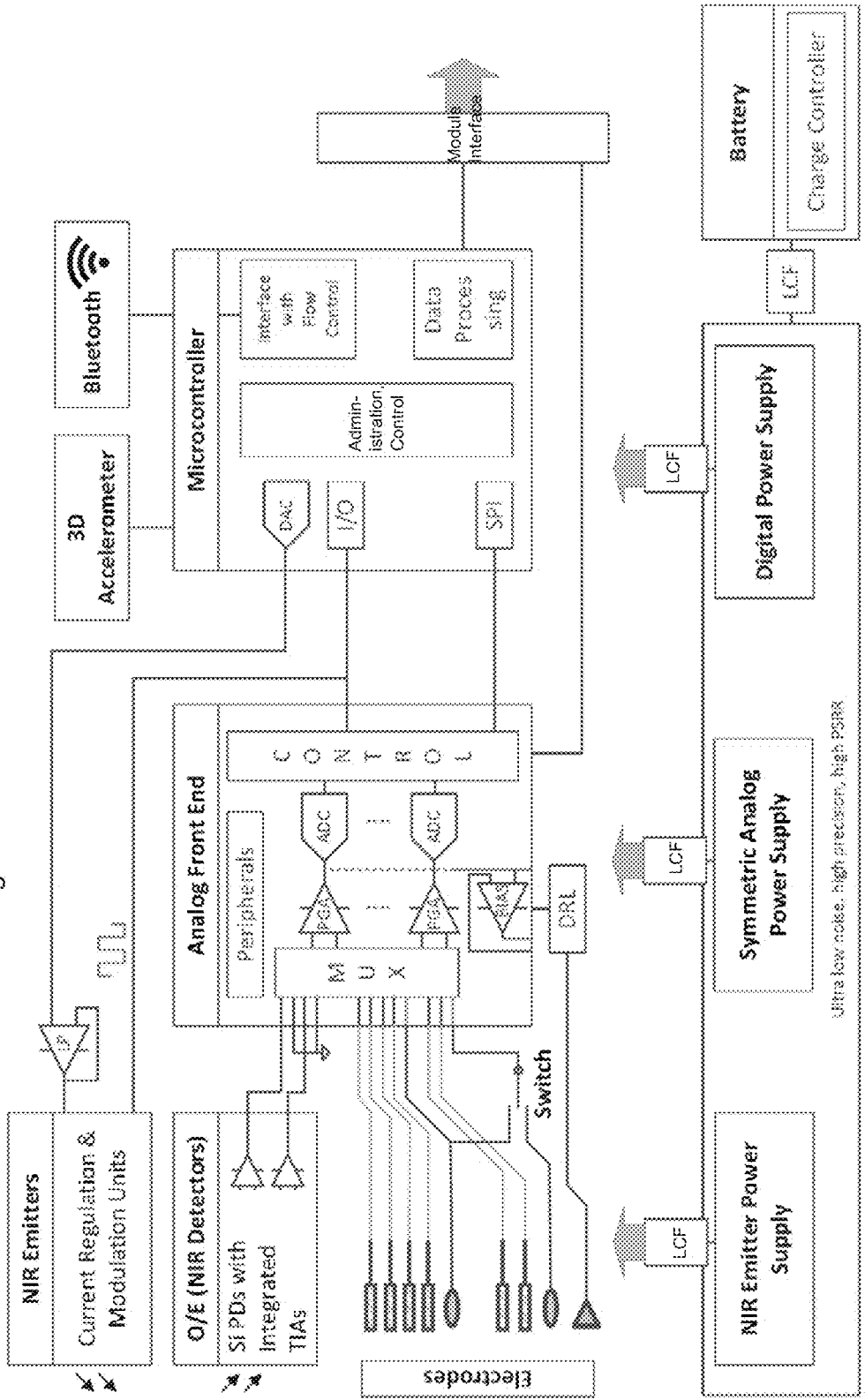
FIG. 2 shows an embodiment of the system hardware architecture comprising an embodiment of the biosignal acquisition device.

FIG. 2 shows a more detailed view of the stand-alone high precision hybrid biosignal acquisition by utilizing a common ultra low noise biosignal AFE and a powerful Cortex M4 microcontroller together with improved fNIRS emitter and detector units from the open fNIRS design (see Luehmann et al., "Towards a wireless open source instrument: functional Near-Infrared Spectroscopy in mobile neuroergonomics and BCI applications", Frontiers in Human Neuroscience, 2015, volume 9, no. 617). There are 4+2 differential bio-potential inputs (blue: measurement, orange: switchable reference, green: ground (configurable Driven Right Leg)). All critical components are buffered and supplied individually by ultra low noise, high power supply rejection ratio (PSSR) low drop-out regulators (LDO) from a charge-controlled Li-Ion Battery. Communication and data transfer via integrated Bluetooth module.

When designing a new generation miniaturized hybrid instrument for bio-electrical and bio-optical measurements, attention has to be paid on how to implement these hybrids such that high precision can be achieved and crosstalk between the signals and crosstalk from digital components in the mixed-circuit design are minimized.

Here, essential advantages of unified hybrid approaches opposed to the combination of two separate instruments are both the synchronicity of the acquisition and a common ground that allows more sophisticated consideration of current paths and fields to minimize noise and electrical cross-talk. Especially considering miniaturization and precision aspects in a mixed-circuit design, this is solved by using a known Analog Front-End (AFE) integrated circuit for both signal types:

The M3BA hardware architecture is based here on the high precision circuit ADS1299 (see Datasheet ADS1299 Low-Noise, 8-Channel, 24-Bit Analog Front-End for Biopotential Measurements from Texas Instrument), which is a very low-noise (1 $\mu V_{pp}$ (70 Hz BW)) 24-Bit Delta-Sigma AFE with 8 differential inputs optimized for EEG biopotential measurements.

It provides many peripheral features such as programmable gain amplifiers (PGAs, G=1-24), configurable sample rate (250 SPS-16k SPS), a built in bias-drive amplifier and a multifunctional input multiplexer (MUX).

The AFE is embedded in a framework made up of a powerful 32 Bit ARM Cortex M4 microcontroller and enhanced functional units for near-infrared (NIR) light emission and detection, that are inspired by a modular open fNIRS technology (see Luehmann et al. 2015 cited above for more details).

The configurable NIR light emitter units use dual-wavelength LEDs with 750/850 nm (Epitex L750/850-04A) that are stabilized and modulated by custom high precision OpAmp and FET-based current regulator/modulator circuits. This increases accuracy and robustness against radiation intensity fluctuations due to voltage variations or semiconductor junction temperature changes—and enables square-wave modulation for phase-sensitive (lock-in) detection of the optical signal.

The NIR light detector units are based on Si-photodiodes (Burr-Brown OPT101) with integrated trans-impedance amplifiers (TIA). The selection is a tradeoff between safety and minimization aspects (lower supply voltages and smaller size), responsivity (0.45 A/W @650 nm), noise minimization and bandwidth (14 kHz) for phase-sensitive detection. In the openNIRS design, the analog detection was based on an analog lock-in detection circuit. Here, the attenuation by phase shifts, size, cost and number of components is minimized by performing phase-sensitive demodulation on the microcontroller in the digital domain.

The eight differential AFE signal inputs are split into 2 channels that measure the single-ended optical time division multiplexed fNIRS signal against analog system GND and 4+2 differential bio-potential channels that are measured against a split or common reference (selectable via micro switch). In this way, the AFE fuses the high precision measurements of both analog signal types. Configuration, control, processing and communication tasks are performed by the Cortex M4 microcontroller running at 120 MHz with an external crystal for jitter minimization. In particular, it performs

- data processing and retrieval from AFE and Accelerometer (via SPI);
- configuration of AFE (PGA, MUX, sample rate, etc.),
- adjustment and modulation of NIR LED currents/intensities. For adjustment, a filtered internal 12 Bit DAC signal is used as regulator command variable.
- control of NIRS channels and timing (see next subsubsection), digital lock-in demodulation of optical signals,
- communication with PC (via flow controlled and ring-buffered USART bluetooth module) and with other modules (physical interface for timing and control),
- power management and supply control.

For minimization of noise and electrical crosstalk between analog signals but also between the analog and digital circuits, the architecture was carefully designed considering the best practice for mixed-signal, multi-layer and multi-power supply designs. To maximally decouple the functional analog and digital units in the instrument, the LED-emitter units, the bipolar analog detector and AFE circuits and the digital components (microcontroller, accelerometer, digital AFE side, etc.) are supplied separately by ultra low noise, high precision and high PSRR low drop out regulator based power supplies and are additionally buffered with LC- and ferrite low-pass filters.

The 6 layer PCB was lay-outed with split analog, digital and supply/GND planes, shielding, via stitching and return current optimization techniques, amongst others.

Figure 10:
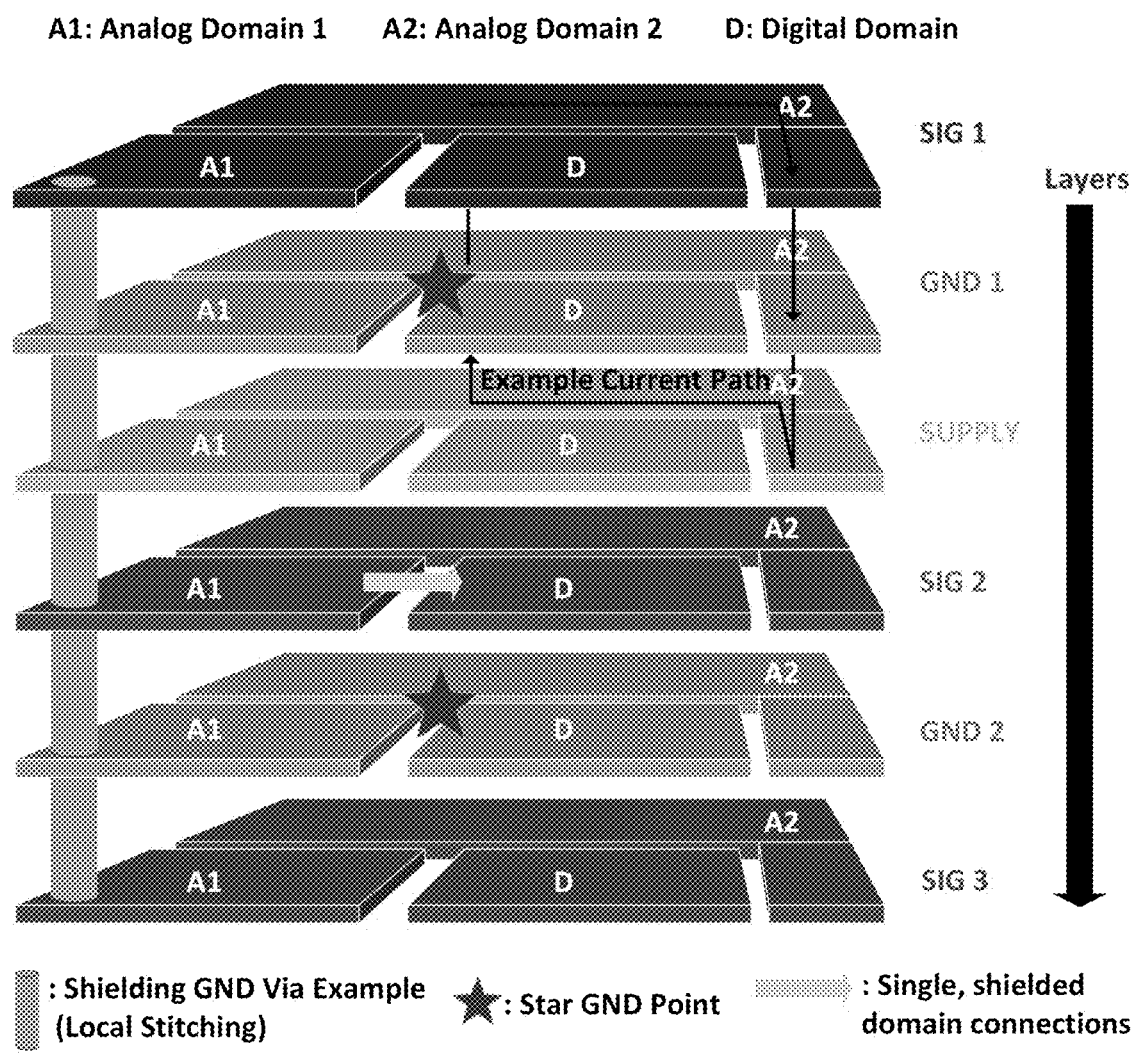
FIG. 10 shows a schematic view of different layers in the circuit design/board layout.

In FIG. 10 layers for an embodiment with different means to decouple domains by different measures are shown. In other embodiments not all of those measures have to be present at the same time.

The instrument is supplied by a single replaceable Li-Ion Battery and has an integrated charge controller for fast recharging via USB. With M3BA being completely wireless and running on voltages<3.7 V, user safety and power consumption issues are dramatically decreased.

Figure 3:
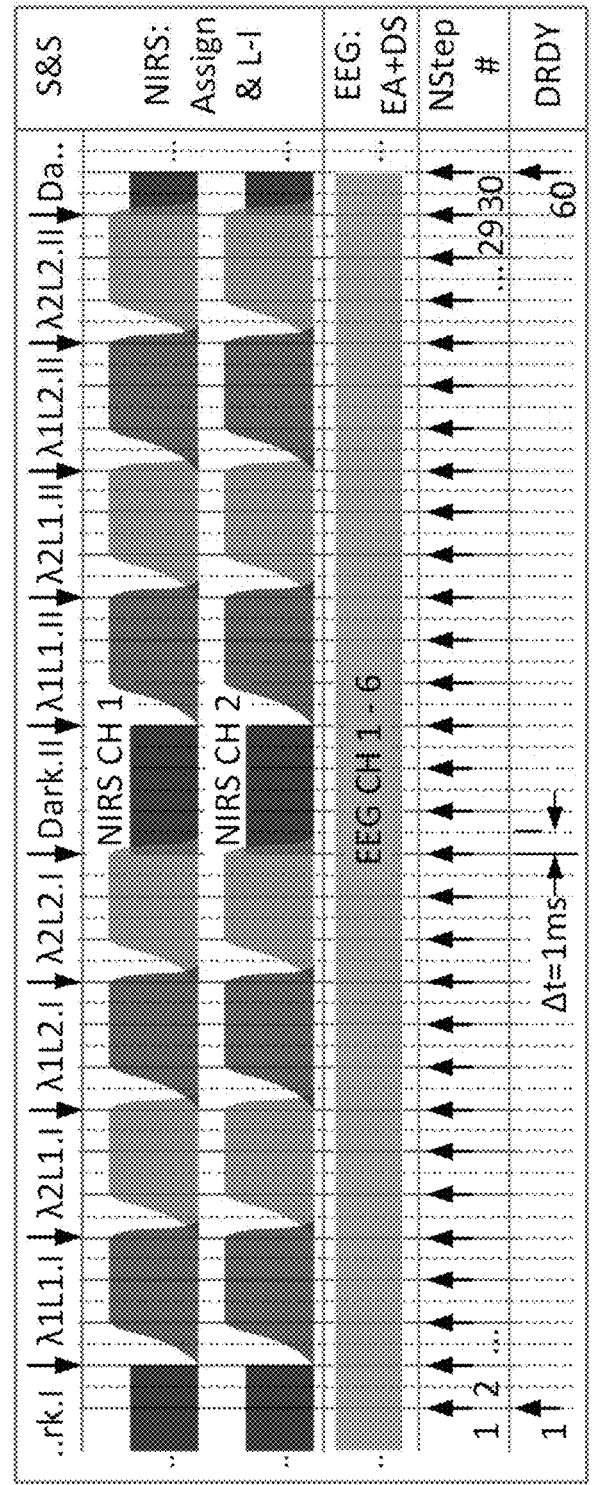
FIG. 3 shows a hybrid NIRS and EEG acquisition timing scheme for a single module of an embodiment of the biosignal acquisition device.

Hybrid acquisition, timing and communication: To administrate and synchronize the acquisition of both signal types, the AFE and microcontroller (μC) build a closed loop in the M3BA architecture. Once a continuous measurement is started, the AFE acquires signals with a sample rate previously set (using an internal oscillator) and indicates complete conversions to the μC via a Data Ready (DRDY) signal. The DRDY signals trigger data retrieval and time division multiple access (TDMA) control of the fNIRS emitters/detectors by the μC. FIG. 3 exemplifies such a typical hybrid acquisition cycle of a single M3BA module.

From bottom to top of FIG. 3:

DRDY: Data Ready signal of AFE sampling all channels with 1 kSPS;

NStep #: iteration of NIRS administration routine for one complete measurement for all active channels (here: 4);

EEG: EA+DS: Exponential Averaging and DownSampling of EEG signal;

Assign L-: Assignment of emitter-detector combinations to channels and lock-in extraction;

S\S: Sample and Switch on/off new wavelengths (Δ)/ LEDs (L).

The AFE runs at a fixed sample rate of 1 kSPS (with an input bandwidth of BW=262 Hz); one complete NIRS measurement cycle takes 60 sample (DRDY) events. While the EEG data is continuously saved, exponentially averaged and downsampled to a user-configurable sample rate of 500 or 250 SPS, the NIRS routine is called every second DRDY iteration. In one NIRS measurement cycle, it subsequently switches twice (I/II) through all available emitter states (here five: two LEDs $L_{y=1}$, and $L_{y=2}$ each with two wavelengths $\lambda_{x=1}$=750 nm and $\lambda_{x=2}$=850 nm and a dark measurement period).

For one module, each state is sampled 6 times, where at least the first two samples are discarded during settling of the Si-PD signal ($t_{dwell} \geq 2$ ms).

The last of the acquired samples is saved, assigned, and the next emitter state is activated. Once each 60 ms, when a NIRS measurement cycle is finished, all resulting four measurements of each emitter/detector pair (2 active emitter and two dark measurements) are combined in a lock-in extraction step ($\lambda_x L_y^I + \lambda_x L_y^{II}$-Dark$^I$-Dark$^{II}$) for dark current and background radiation subtraction. This results in an fNIRS sample rate of $f_{sNIRS}$=1/60 ms=16.66 Hz with the fNIRS samples being time-locked to the EEG signal. Since each emitter state is activated two times per measurement cycle, this yields a LED current switching frequency of $f_{switch}$=33.33 Hz and its multiples. The resulting electrical crosstalk into the EEG inputs was minimized by the above mentioned design practices and evaluated.

For synchronization of several M3BA modules, one declared master module shares a physical 8-wire parallel interface with the slave modules. Over this interface, all AFEs are synchronized with a shared sample clock provided by one master AFE; fNIRS TDMS channel control is administrated and common references are shared.

Communication of each module with a host PC is done via an integrated Bluetooth module (BTM) from ST-Microelectronics (SPBT2632C2A). Data between μC and BTM is communicated via flow-controlled and ring buffered USART interface to minimize packet loss.

Hardware Performance Characterization

In this subsection, methods and phantoms used for evaluation of the hybrid architecture are presented. Since the ADS1299 is designed for EEG-acquisition and performance details are provided by the manufacturer, we focus on the optical fNIRS and hybrid performance as well as crosstalk characteristics.

Evaluation of fNIRS signal quality and phantom: The evaluation of the optical characteristics was performed employing a solid homogeneous optical phantom with tissue-like optical scattering and absorption properties, to mimic (1) the total attenuation that occurs in the tissue at a source-detector separation of 30 mm, (2) the diffuse nature (in terms of its spatial and angular distribution) of light exiting the tissue.

A phantom of known diffuse transmittance was used and that was devised and characterized to assess the responsivity of the detection system of time-domain optical brain imagers (see Wabnitz et al., Performance assessment of time-domain optical brain imagers, part 1: basic instrumental performance protocol, J. Biomed. Opt., 2014, volume 19, number 8, pages 086010; Wabnitz et al., Characterization of homogeneous tissue phantoms for performance tests in diffuse optics, Proc. SPIE 2016, volume 9700).

As a measure of diffuse attenuation the "optical loss" (OL) as defined in the international (IEC/ISO) standard for functional NIRS equipment (see Medical electrical equipment—Part 2-71: Particular requirements for the basic safety and essential performance of functional near-infrared spectroscopy (NIRS) equipment, IEC/ISO, IEC 80601-2-71: 2015) was adopted, i.e. as the ratio of the total optical power exiting a circular aperture of specified diameter (8 mm) on the exit side of the phantom and the power injected on the entrance side.

In the following, the optical loss is either given as a ratio (OL) or in dB units, where X dB optical loss is equivalent to $10^{-X/10}$. The optical loss of the phantom used was 24.7 dB at 750 nm and 23.5 dB at 850 nm. The tests in the IEC/ISO standard refer to optical losses of >40 dB or >60 dB, depending on the particular test, to mimic a typical attenuation for fNIRS. Such values were achieved by using additional gray filters.

The tests were performed in a custom experimental setup with one fNIRS emitter-detector pair and the phantom in transmission geometry, as shown in FIG. 4A.

Figure 4B:
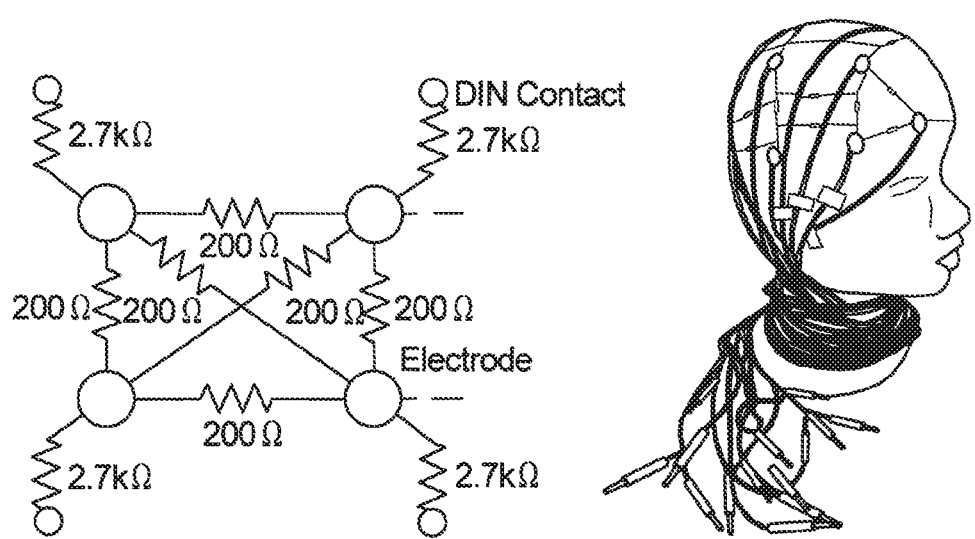
FIG. 4B shows an electrical phantom.

FIG. 4A shows an experimental setup for optical fNIRS characterization using an optical phantom with neutral step filters. FIG. 4B shows an electrical phantom for crosstalk-evaluation of fNIRS switching into EEG-inputs of M3BA and a commercial device.

The phantom was placed in a black plastic holder, with its bottom surface in direct contact with the fNIRS photodetector. On the top side, the phantom holder case was closed with a custom black two-piece lid (3D-printed) that acted as a rail for an absorbing neutral step filter (15 steps covering an optical density range of approximately 2 orders (20 dB)) and additional neutral density glass filters. These filters were used to vary the overall optical loss. Light from the NIR emitter mounted on top of the structure was imaged onto the phantom (diameter of illuminated spot: 5 mm) by two convex lenses and passed through a controllable optical shutter (type Melles Griot 04 IES 211 with controller 04 IPS 850, shutter speed: 60 ms). The shutter was controlled via a M3BA hardware-trigger output and shutter (de-)activation was acquired and labeled to the acquired NIRS data stream. The attenuation of all used neutral grey filters and steps were determined independently via power transmission measurements using a supercontinuum laser (SC500-6, Fianium Ltd, UK) with acousto-optic tunable filter tuned to 750 nm and 850 nm, respectively, and a Coherent Fieldmaster power meter with sensor head LM-2.

The following measurements were conducted with an input gain setting of G=4 and an emission level setting of I=8 (8.94 mW @ 750 nm, 8.34 mW @ 850 nm):

Drifts/Stability: At a fixed total optical loss ($OL_{750\ nm}$=47.3 dB, $OL_{850\ nm}$=50.2 dB), the optical signal was acquired continuously for 15 min twice. For estimation of the continuous drift, the slope and $R^2$ of a linear least squares fit were calculated.

Signal to Noise Ratio (SNR)/Coefficient of Variation (CV) and Linearity (LIN) of the instrument: In a continuous acquisition, after 5 min free-running for warm up, 42 measurements of the NIR signals in a range of $OL=4\times10^{-2}-9\times10^{-6}$ (26.0 dB-69.5 dB) were conducted in approx. 1.5 dB steps. The last 10 s of data (170 samples) were used for the evaluation of each step. During manual filter step transitions, the shutter was closed. For each measurement, the shutter was opened, thus also providing a Step Response (SR) in the acquired optical/voltage signal s. Standard deviation ($\sigma_s$) and mean ($\overline{m}_s$) were calculated for all steps and both acquired wavelengths. CV and SNR were calculated as $CV_s=\sigma_s/\overline{m}_s$ and $SNR_s=20\ \log(\overline{m}_s/\sigma_s)$. It should be noted that for hardware performance characterization this SNR is related to the total optical signal, not to the hemoglobin concentration changes derived in fNIRS. For LIN evaluation, slopes and $R^2$ values of linear least squares regression fits on the $\overline{m}_s$ for each wavelength were calculated.

NIR Emitter Power: The continuously emitted radiant power (no switching) for each wavelength was measured with a Coherent Fieldmaster power meter with measurement probe LM-2. The LED was mounted in such a way, that the illuminated area was fully covered by the measurement probe surface. The emitted power at 6 different current levels ($(5-10)\times10$ mA) and the illuminated area on the optode surface were measured to determine the incident intensity at the subject's scalp.

NIR Emitter Spectrum: The spectra of the NIR emitters for both wavelengths and different current levels were measured with an Avantes AveSpec 3648 spectrometer with an integration time of $t_i$=50 ms and averaging over 200 measurements. The NIR light was attenuated by 32.4 @ 750 nm and 33.3 dB @ 850 nm using neutral density filters. The measured spectra were corrected by the previously determined calibrated spectral sensitivity and by dark measurements. Spectral dependence on emission directions due to varying local semiconductor characteristics was evaluated by measuring the spectra at different tilts of the emitter. Peak wavelengths (PW) were calculated by a maximum search of a Gaussian fitted to the top 10% area of each spectrum. Maximum PW shifts over all intensities were determined ($\Delta PW_{\lambda,max}$). The Full Width at Half Maximum (FWHM) of the spectral power distribution was calculated as the difference of the wavelength between the two points whose corresponding power values are equal and 3 dB lower than the values at each peak wavelength.

Noise Equivalent Power (NEP): For determination of the NEP of the NIRS part of the instrument, 60 s (1000 samples) of the signal were acquired for each input gain G, while the fNIRS emitters were active but the detectors were put into an opaque box with no incident light. Using the OPT101 responsivities $R_{\lambda=750}$=0.55 V/µW and $R_{\lambda=850}$=0.60 VON, the signal mean $\overline{m}_{G\lambda}$ and std $\sigma_{G,\lambda}$, the NEP was then calculated for the full input bandwidth (262 Hz as $$262\ \text{Hz as}\ NEP_{G\lambda} = \frac{\overline{m}_{G\lambda} + \sigma_{G\lambda}}{R_\lambda G}$$

Evaluation of electrical signal quality and phantom: For comparative measurements of fNIRS switching crosstalk into EEG inputs a resistor network made from metal film 0.1% resistors as shown in FIG. 4B was used. The phantom consists of a polystyrene head covered with a resistive network with nodes ("electrodes") at 10-20 EEG-positions, which can be accessed via DIN-electrode jacks. The resistive network simulates electrode-to-skin impedance (2.7 kΩ) and between-electrode skin conduction (200Ω). Clearly, this network does not have the same AC properties as the human scalp probed with EEG. At position F8, voltage divided sine signals with A=150 µV and $f_s$={1, 10, 100} Hz from an Agilent 3500B signal generator were fed into the network. The two NIR emitters of one M3BA module were placed between Fz & Cz and F3 & C3 and either active or inactive (a=(0,1). Signals were measured at positions p={Cz, Fz, C3, F3, F8} against a common reference (GND) at T5. Each 70 s measurement $m_{f,p,a}$ was repeated with both the M3BA module (@500 SPS) and with a commercial reference EEG amplifier for comparison (COM, g-tec USB Amp, 2009, @512 SPS). For evaluation of the crosstalk, the FFT power spectra of the last 60 s of the $m_{f,p,a}$ were calculated and normalized for the peak power at $f_s$ to be one: $P_{norm}(f_s)$=1. Then, for i=1 . . . 7, the normalized noise powers of multiples of the fNIRS switching frequency $f_{switch}$ were extracted and summed up $P_{noise}=\Sigma\ P_{norm}$ (i $f_{switch}\pm0.155$). This allows a comparison of the strength of NIRS switching noise introduced into the EEG signal.

Crosstalk/electrical noise from NIRS currents can be introduced to the inputs on the PCB itself when the instrument layout, for instance current return design, is not optimal—but can also be coupled in by fields between the EEG-electrode and NIRS optode wires. To differentiate between both types, we used a feature of the ADS1299 AFE that allows the input multiplexer to internally shorten the inputs to measure the input-referred noise. For active and non-active NIRS (I=8) and all PGA gains G=1-24, the input referred noise was determined by calculation of the standard deviation of 2000 samples (@500 SPS) for each condition.

To verify the desired EEG input linearity and cut-off (mainly influenced by the AFE input bandwidth and implemented exponential averaging on the µC), the input frequency response was evaluated by acquiring a linear 5 s sweep from 0.1 Hz-2 kHz with constant step width and 100 $mV_{pp}$ amplitude, generated by the Agilent 3500B. The frequency response was extracted by applying a polynomial curve fit with order 21 through the Hilbert envelope of the acquired raw sweep signal.

All experiments were conducted in a magnetically and electrically shielded room (two-mu meta layer Ak3b, Vakuumschmelze, Hanau).

Physiological Data—Human Subject Studies

In the following the functionality of the acquisition of the targeted bio-signals is described.

The M3BA fNIRS functionality utilizes a further improved version of the open fNIRS emitter-detector design that has been validated with a mental arithmetics based N=12 BCI study (see above Luehmann et al. 2015).

For the EEG-functionality and multimodal acquisition, the following human subject studies were conducted according to the declaration of Helsinki and approved by local ethics committees. All participants were comprehensively informed and gave written consent before the experiment.

EEG: Comparative Measurements of Auditory Evoked Potentials: To characterize the practical capabilities of EEG amplifiers it is often the best to perform evoked potential measurements with human subjects. Pure technical parameters can be easily determined using proper test equipment, but for EEG signal generation phantoms are rarely known. Instead human subject data are considered the "gold standard".

This qualitative approach and measured auditory evoked potentials (see Picton et al. "Human auditory evoked potentials. I: Evaluation of components", Electroencephalography and clinical neurophysiology, 1974, volume 36, pages 179-190) on five right handed subjects (3 male, 2 female, avg. age 26±2y.) stimulating the left ear with 1 kHz sine tones of 400 ms duration. Tones were delivered using an Etymotic ER-30 (www.etymotic.com) insert earphone and an RME HDSP 9632 (www.rme-audio.de) soundcard. Tones had 92 dB SPL as measured with a Bruel & Kjaer type 4153 artificial ear.

In total, 300 tones were delivered with a randomized inter-stimulus interval of 1.5-2.5 s. This resulted in an experiment time of roughly 12 minutes and after 6 minutes subjects were notified of half time. Each subject was measured with the M3BA and a commercial g.USBamp EEG amplifier (www.gtec.at). The electrode plugs were moved between device inputs and the session lasted 30 mins (12+12+change of EEG plugs) in total for both amplifiers.

The sequence of M3BA and g.USBamp was randomized between subjects. The signals were acquired over the left somatosensory cortex at the 10-20 positions C3, F3, T3, and T5 and measured against the right mastoid with GND (DRL) placed at Fpz. AgCl ring electrodes were used with gel and impedances were below 10 k$\Omega$. The recorded signals were digitally filtered with a zero delay bandpass of 0.1-45 Hz and a Butterworth 4th order characteristics. Epochs were baseline corrected in a 100 ms pre-stimulus interval and then averaged for each subject and channel to obtain the AEP. The obtained AEPs were compared to literature results (see Picton et al. 1974) with respect to amplitude and latency of the N1-P2 complex.

Raw multimodal example: For qualitative example data and validation of the multimodal mobile acquisition capabilities of the M3BA instrument a simple 10 trial experiment was performed on one subject: One single M3BA module was fixated to an 10-20 EEG cap (easycap) simultaneously measuring EEG (@500 Hz) with wet electrodes at positions O1, O2, Cz and Fp2, one channel of ECG (Einthoven 2 derivation), accelerometer data and 4 fNIRS channels (@16.6 Hz).

fNIRS emitters were placed at AF3 and AF7, detectors at F5 and Fp1, resulting in $\approx$30 mm emitter detector distances. The freely moving subject was asked to stand, close eyes and take a deep breath when a first beep sound was played and to open eyes after a second beep sound after 10 s. For a better assessment of the raw data quality, limited processing was performed in MATLAB: EEG and ECG channels were digitally filtered with a 6th order zero delay 0.1-45 Hz Butterworth bandpass. For alpha-band power estimation during eyes closed, the average of the Hilbert envelopes of the bandpass filtered (Butterworth 2nd. order, 10-13 Hz)

signals of O1 and O2 were calculated. fNIRS O2HB and HHB concentration changes were calculated from the raw optical signal using effective extinction coefficients (see Zhang et al., "Experimental comparison of using continuous-wave and frequency-domain diffuse optical imaging systems to detect heterogeneities", in "BIOS 2001 The International Symposium on Biomedical Optics", 2001, pages 219-238, International Society for Optics and Photonics) for the measured LED spectra and HOMER2 (see Huppert et al., "HomER: a review of time-series analysis methods for near-infrared spectroscopy of the brain", Appl. Opt., 2009, volume 48, no. 10, pages D280-D298, April) software and were then baseline corrected by mean subtraction.

Results

Figure 5:
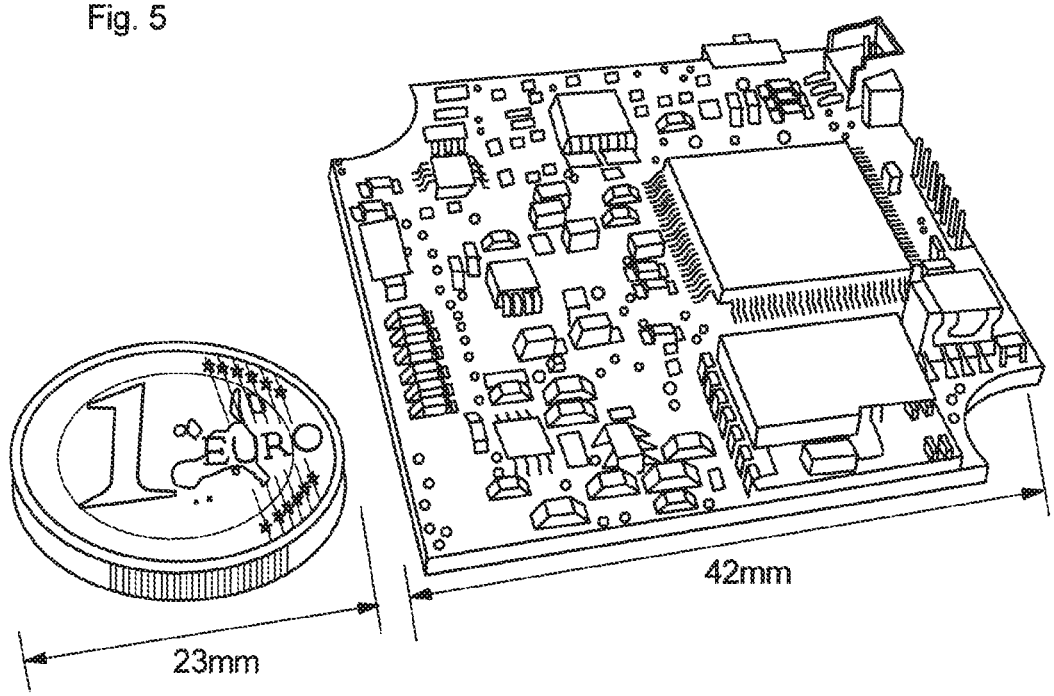
FIG. 5 shows a standalone M3BA module without battery comprising an embodiment of the biosignal acquisition device.

The Mobile, Modular Multimodal Biosignal Acquisition (M3BA) architecture was implemented successfully in a highly miniaturized design for precision EEG, EMG, ECG and fNIRS acquisition, that can be used—amongst others—for WBSN based hybrid BCI scenarios. The dimensions of one fully standalone M3BA module (see FIG. 5) are only $4.2 \times 4.2 \times 0.6$ cm$^3$. This allows a flexible integration in different mechanical set ups and head-and-body-gears.

When directly connected to the module's edges, NIRS source-detector distance is 35 mm. Different sizes/capacities of Li-Ion batteries can be connected via a standard connector: With a current consumption of <100 mA (all features active), a module runs more than 3 hours on a tiny $28 \times 34 \times 2$ mm$^3$ (300 mAh) Li-Ion battery or more than 18 hours on a standard mobile phone battery.

Table 1 summarizes the system characteristics of the standalone M3BA modules. In the subsequent sections results from the technical tests and from the physiological recordings will be described in more detail.

TABLE 1

| EEG/EMG/ECG/... | |
|---|---|
| # of Channels: 4 + 2 | Resolution: 24 Bit |
| Sample Rates: 500\|250 Hz | Common Mode RR: −110 dB |
| Inp. ref. Noise: 1.39\|0.98 $\mu V_{pp}$ | Input PGA: G = 1 − 24 |
| Inp. Bandwidth: 210\|100 Hz | Config. Driven Right Leg (DRL) |
| fNIRS | |
| # of Channels: 4 + 2 | Resolution: 24 Bit |
| Sample Rate: 16.6 Hz | Wavelengths: 750\|850 nm |
| Emitter lvl.: I = 5 − 10 | NEP: 5.92\|4.77 pW$_{pp}$ |
| Input PGA: G = 1 − 24 | SiPD Respons.: $0.55 \mid 0.6 \frac{V}{\mu W}$ |
| Optical Drift: $< 1.6 \frac{ppm}{\partial}$ | $\Delta PW_{max}$: 4.75\|3.75 nm |
| Optode Dist.: 35 mm/conf. | FWHM: 16.6\|21.4 nm |
| SNR (10$^4$ OL): 66 dB | Intensities$_{750nm}$: $0.07 - 0.14 \frac{mW}{mm^2}$ |
| SNR (10$^6$ OL): 40 dB | Intensities$_{850nm}$: $0.07 - 0.13 \frac{mW}{mm^2}$ |
| Full linearity (10$^{-2}$ − 10$^{-7}$ OL) | Digital Lock-In Amplification |
| Accelerometer | |
| # of Channels: x, y, z | Resolution: 10-13 Bit |
| # Sample Rate: 0.1 − 1k Hz | Ranges: ±2, 4, 8, 16 g |

TABLE 1-continued

| General | |
|---|---|
| Power consumption: <360 mW | Li-Ion Cell (replacable) + charger |
| Bluetooth range: Indoor 5 m | Modularity: Up to 4 modules |
| | Hardware trigger precision: 2 ± 1 smpl |

Optical Characteristics

The drift measurements revealed the necessity of a warm up time of max. 5 min after switching on, in which the emitted 850 nm power settles by 1.7%. After that, the optical signals drifted less than 27.5 nV/s, which in relation to the signal amplitude at ~40 dB optical loss is less than 1.6 ppm/s. The performance characteristics of the fNIRS/EEG unit are shown in FIG. 6A to 6D.

Figure 6A:
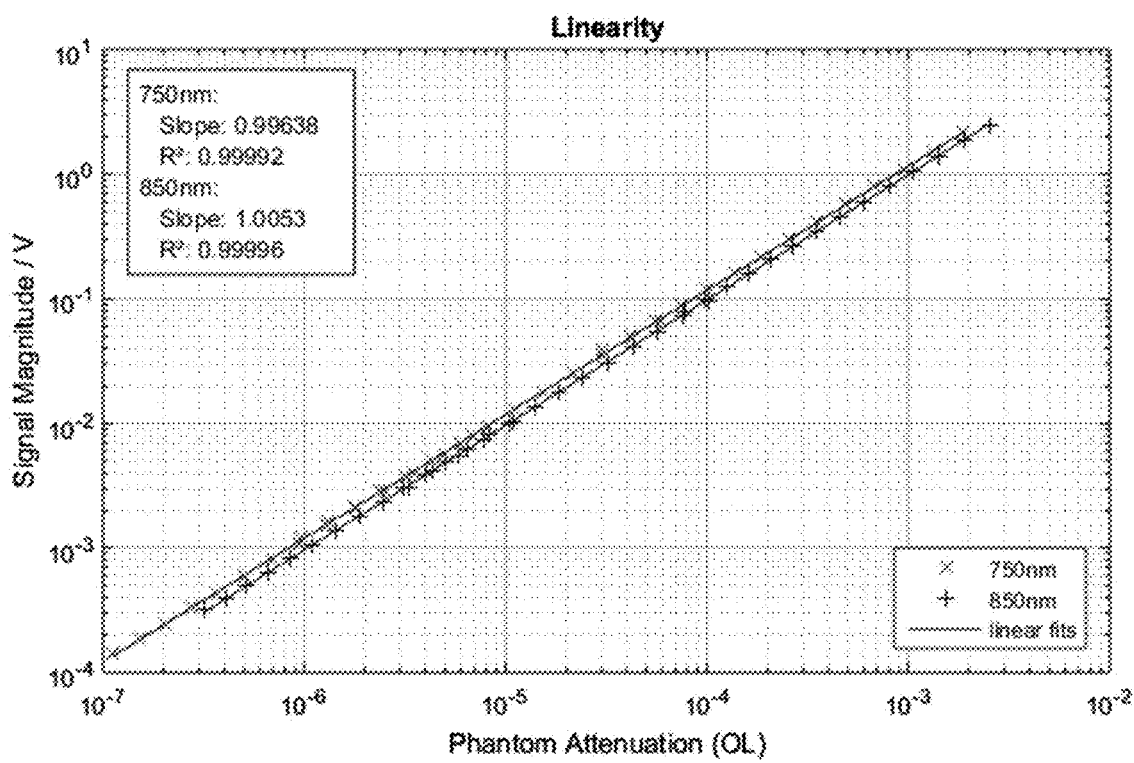
FIG. 6A, FIG. 6B, FIG. 6C, and FIG. 6D show performance characteristics for an fNIRS/EEG unit in connection with an embodiment of the biosignal acquisition device.

FIG. 6A shows the linearity of measured optical fNIRS signals over the whole range of optical loss.

Figure 6B:
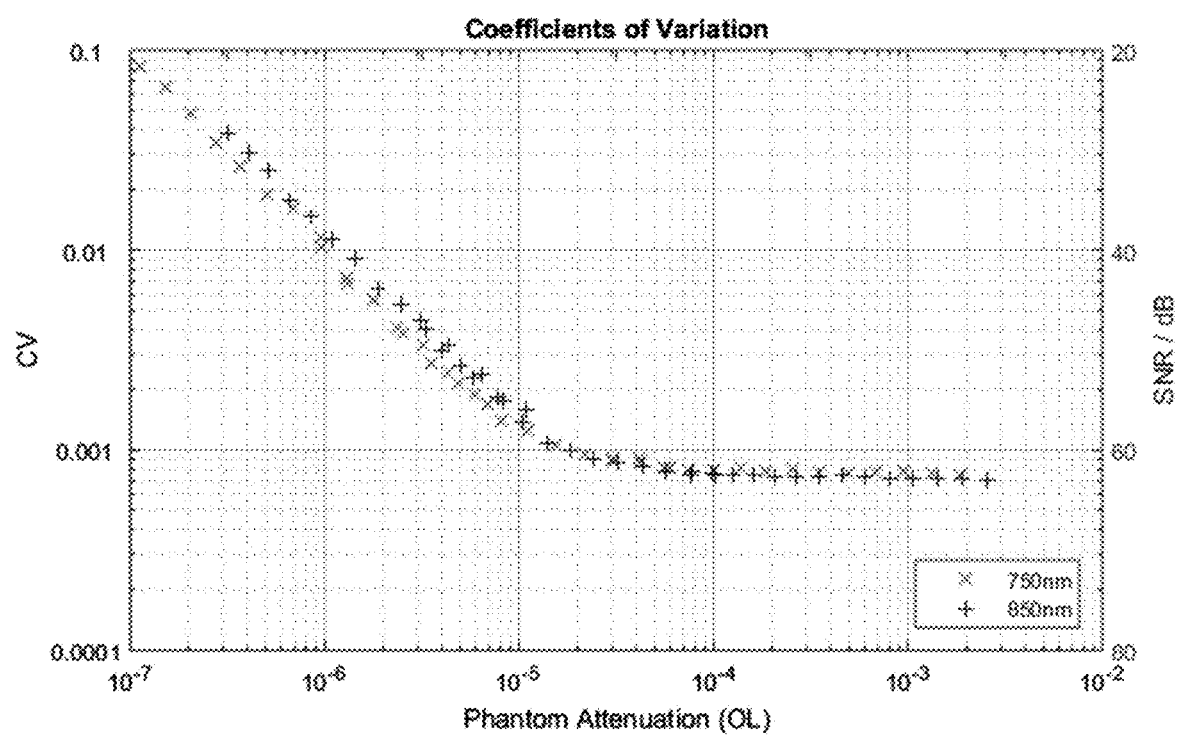

FIG. 6B shows the coefficient of Variation/SNR of fNIRS measurements.

Figure 6C:
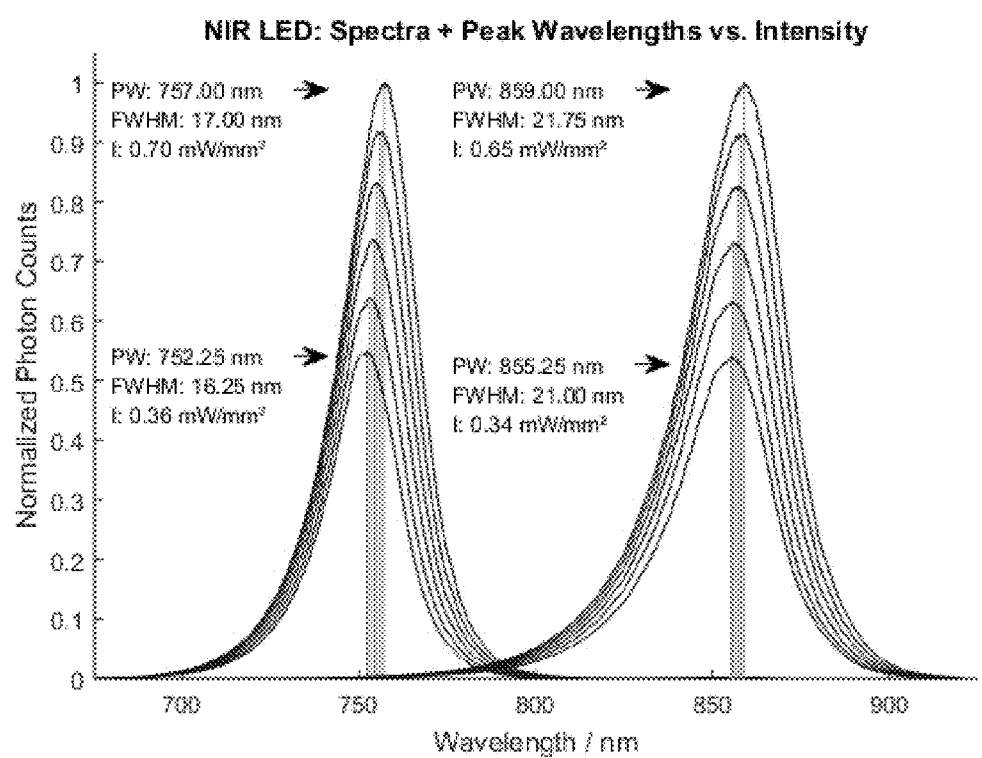

FIG. 6C shows NIR emitter spectra for six intensity levels, min/max peak wavelengths and min/max emitted intensities.

Figure 6D:
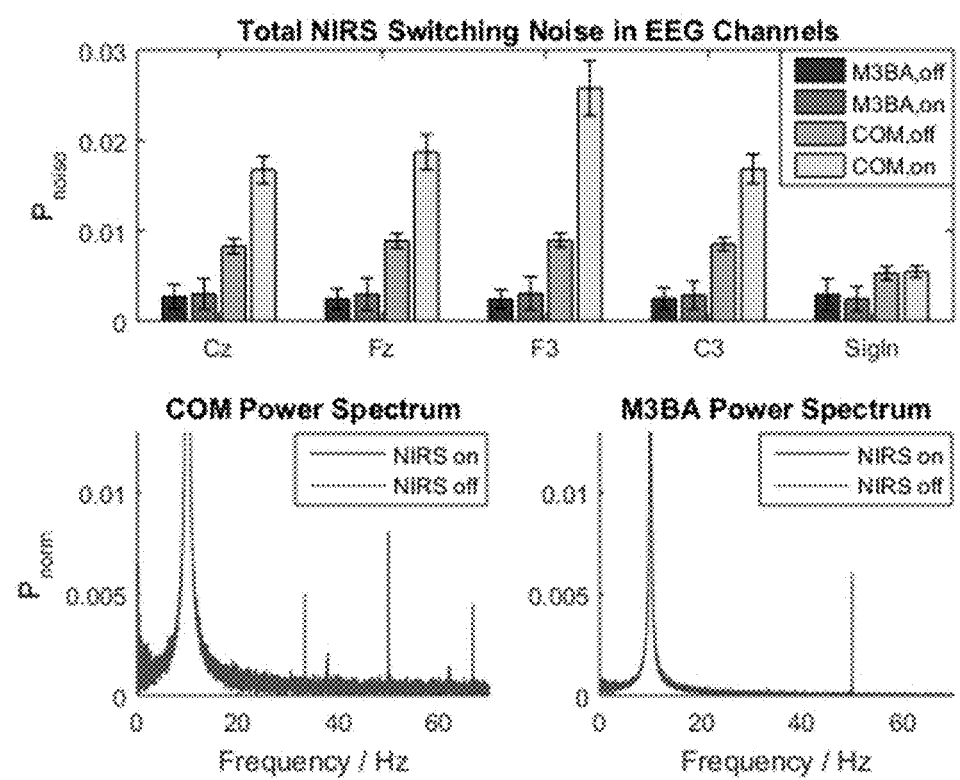

FIG. 6D shows NIRS switching noise in EEG-measurements. Bottom: normalized FFT-Power spectra exemplify presence of $f_{switch}$=33.3 Hz and its multiples in the signals measured with the comparative (COM) device and absence in M3BA. Top: Sums of normalized switching noise fractions for active (on) and inactive (off) fNIRS in the signals of several electrodes.

Some of the optical characteristics are discussed below:

Linearity: The device showed a very distinct linearity (see FIG. 6A) for both wavelengths (slopes $S_{750}$=−0.996, $S_{850}$=−1.005, corr.coeff. $R^2_{750|850}$=0.999) over the full tested optical range.

CV and SNR: The evaluation of CV and SNR for both wavelengths (see FIG. 6B) yielded predominantly constant values (CV<0.001, SNR>60 dB) for low attenuation OL<$5\times10^{-4}$ and linearly increasing CV/decreasing SNR above OL=$5\times10^{-4}$. Even at very high optical losses in the range of $10^{-7}$, the SNR is still about 20 dB, indicating that small changes in optical power occurring in fNIRS experiments can still be measured.

Step responses measured with the shutter for all OL-configurations showed a settling of the signal within one fNIRS sample (60 ms) without further oscillations.

NIR emitter power and spectrum: The normalized spectra of the NIR emitters are shown in FIG. 6C. Tilting experiments did not show a significant dependence between spectrum and tilt of the LED relative to the measurement probe. The spectra, measured for all six implemented intensity levels, show a slight shift towards higher peak wavelengths with higher illumination intensities ($\Delta PW_{750,max}$=4.75 nm, $\Delta PW_{850,max}$=3.75 nm). Changes in the FWHM for both wavelengths are marginal ($\Delta FWHM_{max}$=0.75 nm).

NEP: The Noise Equivalent Power of the detector circuit (the threshold at which incident light of a target wavelength completely drowns in noise) for all PGA gain levels was measured to be in the order of $NEP_{min,\lambda 850}$=4.77 pW to $NEP_{max,\lambda 750}$=5.92 pW incident power.

Electrical Characteristics

Evaluation results for Electrical NIRS switching crosstalk into EEG: Comparative measurements of input referred noise and power supply voltages during active and inactive fNIRS revealed an increase of the high precision bipolar supply voltage noise from 6.6 $\mu V_{mms}$ to 21.4 $\mu V_{mms}$ (262 Hz-BW) when the NIRS was active.

However, the input-referred noise of the EEG channels for all PGA-settings stayed identical to the manufacturers data (0.14 $\mu V_{pp}$, 60 Hz-BW @G=24 and 0.28 $\mu V_{pp}$, 262 Hz-BW @G=24) for both active and inactive NIRS conditions. The crosstalk evaluation on the electrical phantom with both the M3BA and comparative device (COM) (see FIG. 6D) showed distinct peaks at $f_{switch}$ and its higher harmonics in the FFT-power spectra for all test signals measured with the comparative device. Measured with the M3BA module, they are almost completely indiscernible from the generally lower noise floor. This is also reflected in the normalized sums of the fractions of power of $f_{switch}$ and its multiples in measurements during active and inactive NIRS: In the M3BA module, these show no significant deviations and are smaller than 0.003. In the non-hybrid setup with the comparative device, a significant increase between conditions and a noise level up to one order of magnitude (0.028) higher than in the M3BA as well as a spatial dependence can be observed. The higher noise of the COM can be due to longer cable length and unavoidable ground loops as the combined setup was not optimized for low noise performance.

The input frequency responses of the EEG unit for both configurations (250/500 SPS) confirmed flatness (<0.1 dB) in the pass band and the cut-offs set by exponential averaging ($f_{cEA500}$=210 Hz, $f_{cEA250}$=100 Hz) and AFE bandwidth ($f_{cBw}$=262 Hz).

Physiological Data—Qualitative Results

Figure 7:
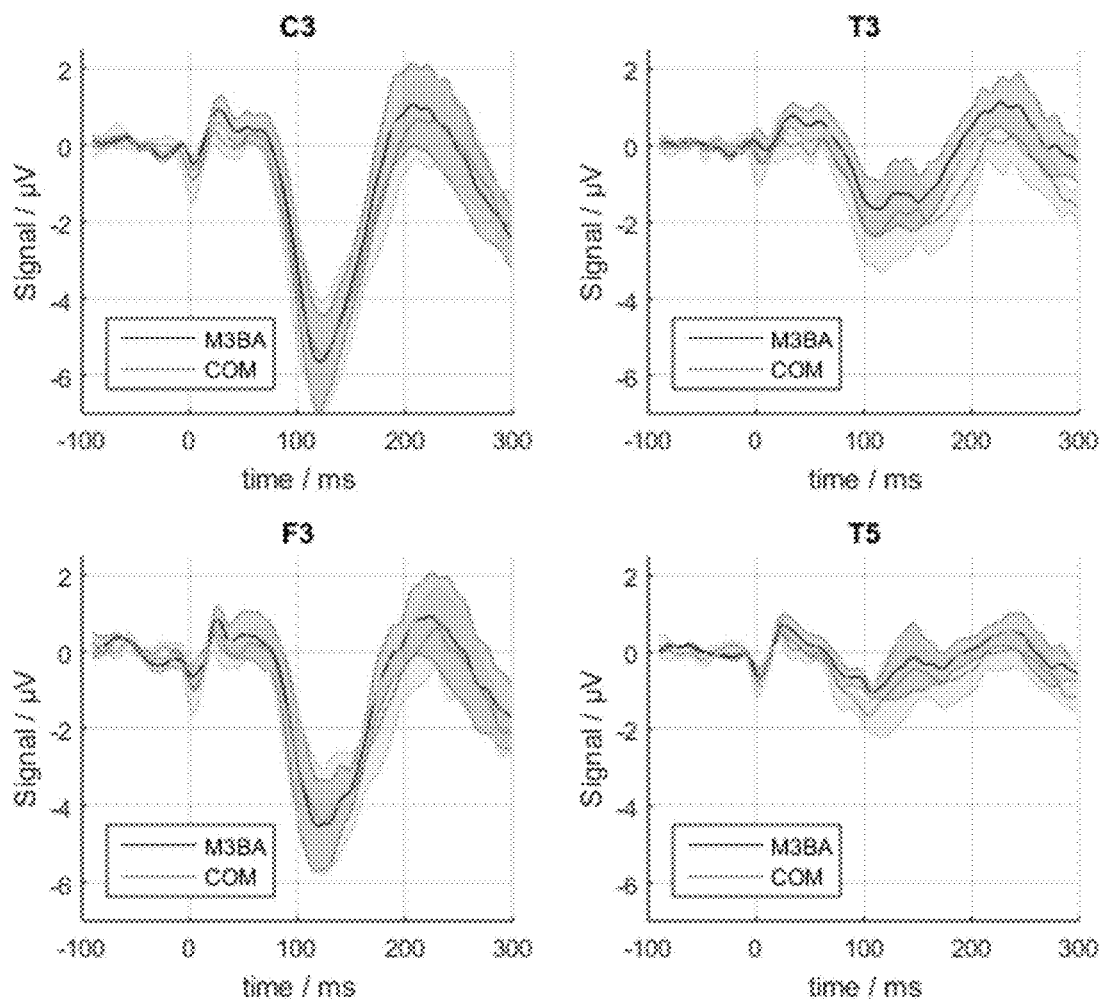
FIG. 7 shows comparative EEG (N100) results between M3BA and a commercial (COM) device.

EEG: Auditory Evoked Potentials: The signals of one of five subjects were discarded due to very high mains hum in the comparative measurement using the COM instead of the M3BA EEG channels. Signal analysis showed distinct N1-P2 peaks typical for AEPs in the EEG signals of all the remaining four subjects. Here, the positions C3 and F3 showed strong N100 amplitudes, where less typical positions (T3 and T5) showed less distinct signals, as expected. FIG. 7 shows the signals of both devices for each channel averaged over all subjects for comparison. The distinct N1-P2 in the signals and their resemblance (regarding timing, amplitude and shape) indicate that indicate that the M3BA performs like a standard precision EEG recording unit.

In FIG. 7 N100 comparative results between M3BA and commercial (COM) device are shown. The solid lines are signals averaged over all subjects, shaded error bars indicate standard deviation between subjects for each channel.

Figure 8:
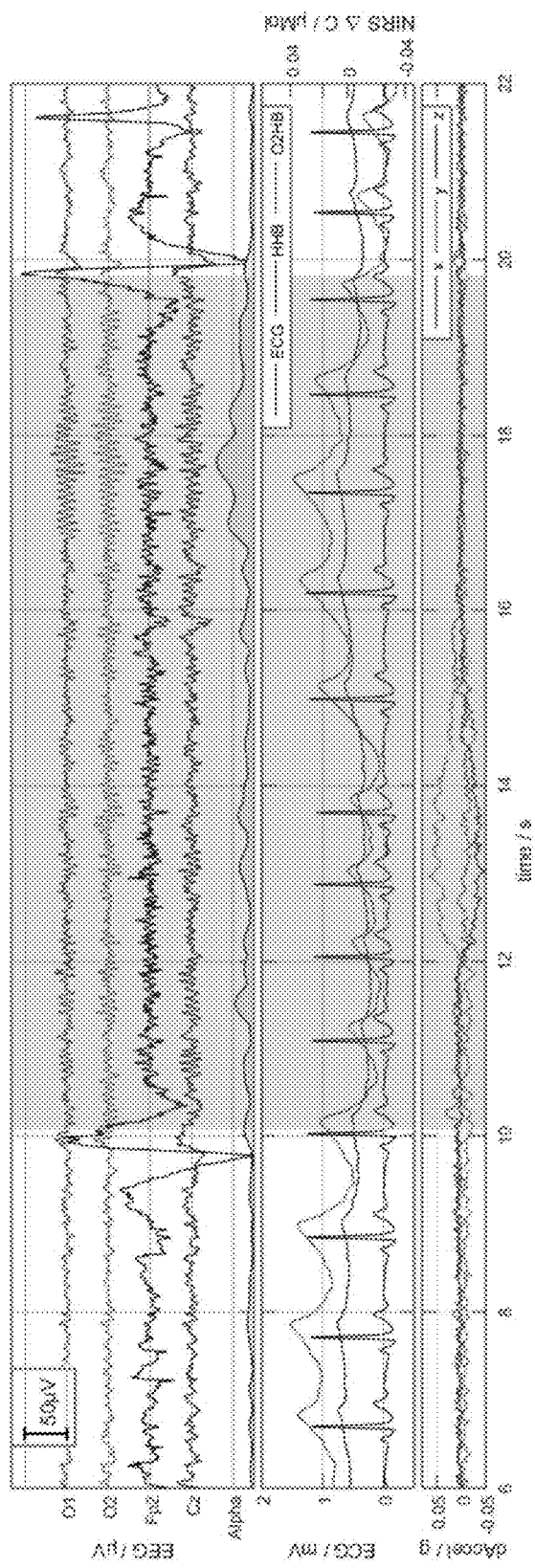
FIG. 8 shows synchronously recorded raw multimodal data from one M3BA module in a freely moving subject during deep breath and eyes open/closed.

Raw multimodal example: FIG. 8 shows a typical single trial of the raw multimodal dataset acquired in the qualitative experiment with a freely moving subject using one M3BA module. It shows synchronously recorded raw multimodal data from one M3BA module in a freely moving subject during deep breath and eyes open/closed: EEG channels and alpha power (top), ECG and NIRS signals (only Ch1 (AF3-F5) for better overview) (mid) and accelerometer signal (bottom). Some typical dependencies between modalities are already easily observable in the raw ECG, fNIRS and accelerometer signals (R- and pulse wave correlation, ECG/NIRS modulation by breathing (accelerometer).

O1, O2, Cz and the alpha channel show clear alpha activity during eyes closed (10-20 s), Fp2 shows typical eye blinking artifacts. Deep breathing in and out is clearly visible in the accelerometer signal. Also, the deep breath impacts the ECG heart rate and R-wave amplitude as well as the overall fNIRS signals. The fNIRS signals show the typically stronger pulse waves in O2HB compared to HHB, which are also clearly correlated to the electrical activity of the heart in the ECG.

CONCLUSION

The development and evaluation of a so far non-existent M3BA hybrid bio-signal acquisition architecture for mobile BCI applications is described herein. The embodiments shown integrate fNIRS with high-precision bio-potential measurements utilizing a shared Analog Front-End. The M3BA instruments were successfully designed for miniaturized (4.2×4.2×0.6 cm$^3$) mobile wireless use (Bluetooth), high precision/low noise acquisition and user safety.

Modularity and combinability as well as a flexible handling of bio-potential references allow scaling and customization of the number and types of channels and modalities. Since the architecture is based on a powerful microcontroller, the user can easily and quickly change, implement and increase the complexity of programs running on the module. Thus, new approaches such as decentralized on-line feature extraction, adaption and filtering on the modules themselves become possible that enable use in wireless tactile scenarios where sensor information is provided and processed with regard to context information and bandwidth availability on the wireless infrastructure.

The fNIRS functionality implemented in the M3bA architecture improves the open fNIRS design by switching from analog to digital lock-in amplification (no attenuation by phase shifts), stand-alone integration of all hardware into one single unit and by better electrical decoupling and noise minimization: The Noise Equivalent Power for optical measurements was improved by 3 orders of magnitude (M3BA: pW$_{pp}$, open fNIRS: nW$_{pp}$).

To achieve the desired high performance characteristics in all modalities, great care was taken to minimize noise and crosstalk by optimizing the mixed-circuit multilayer and multi power-supply layout for the AFE—µC unit. Crosstalk experiments showed a significantly lower impact of fNIRS switching in the EEG inputs of the instrument compared the comparative EEG device. Using LEDs and SiPDs for the NIR light emission and detection allowed both miniaturization, lower power consumption and voltages and thus safer use compared to lasers and avalanche photo diode (APDs) applications. The M3BA units is supplied with a single 3.7 V Li-Ion Cell that can be recharged via USB and replaced if the desired capacity C$_{batt}$ should be adapted to the maximum runtime needed (t$_{run}$~(C mA)/(100 mA) h).

The TDMA use of the fNIRS channels presents a drawback with regard to the sampling rate when several modules are used together at once. As can be seen in the timing scheme in FIG. 3, due to several unused fNIRS samples in the single module case, up to two modules can be combined, still providing a sample rate of 16.6 Hz. However, when more modules are added, due to the TDMA, the sampling rate is decreased. If necessary in the future, this could be solved by simultaneous illumination with sine-modulated light on different frequencies. This however also significantly increases the power consumption.

Another pitfall arises, when two or more persons, all wearing several M3BA modules in a WBAN scenario, meet on close distances. The interference introduced by the number of bluetooth-transmitters is likely to lead to a high number of lost packages that cannot be buffered. For such scenarios, there are currently no optimal solutions regarding the wireless infrastructure. If the modules should be used in such a setting, other transmission standards like ZigBee (IEEE 802.15.4) and WBAN (IEEE 802.15.6) or even completely new standards would have to be taken into consideration.

An evaluation of an embodiment was performed by taking measurements using an optical and an electrical phantom and internal features of the AFE (For a validation of the unimodal open fNIRS functionality, see Luehmann et al. 2015). EEG functionality was validated by an N=4 AEP user study with both the new and a commercial reference instrument, multimodal acquisition was validated by a qualitative raw data experiment simultaneously acquiring fNIRS, EEG, ECG and acceleration data. The system performance tests showed excellent linearity, low optical drift and very low noise levels amongst others. The noise characterization revealed that between 20-50 dB OL the CV remains constant with values better than 0.1%. This noise component can be attributed to the LED light source; signal as well as noise are proportionally attenuated by the phantom as long as photon noise can be neglected. Above 50 dB OL, CV linearly increases with an approximate slope of 1 which is indicative of the domination of a signal-independent noise component. Extrapolating the course to 80 dB OL yields a CV≈1 for a signal magnitude in the order of 10 µV which coincides with the manufacturer's data for the photodiode's dark noise in the used bandwidth (15 µV-262 Hz BW). This is also in accordance with the measured NEP values in the order of $10^{-12}$ W, when considering the incident optical LED power of $10^{-3}$ W, an OL of $10^{-8}$, additional losses in the optical path and the fact that the actual detector area (5 mm$^2$) is smaller than the area of the 8 mm diameter aperture used in the definition of the optical loss. It is therefore assumed that the signal-independent noise component is the photodetector's thermal noise on which future attempts to improve performance should focus.

The electrical AEP signals measured with the M3BA and the reference device showed the expected characteristic N1-P2 signal amplitudes and shapes.

Further embodiments of the device can comprise M3BA modules with different approaches for robust and spring-loaded mechanical headgear (similar to the open fNIRS approach) and utilization in hybrid mobile BCI studies.

Some items of embodiments are summarized below.

Objective: In the field of telemedicine, neurotechnology and Brain-Computer Interfaces (BCI), hybrid multimodal acquisition technology and signal processing gain momentum. However, currently there are no commercial hybrid devices combining bio-electrical and bio-optical measurements (here Electroencephalography (EEG) and functional Near Infrared Spectroscopy (fNIRS)) that are also miniaturized, customizable and wireless. Our objective was the design of such an instrument.

Approach: We design and evaluate a hybrid mobile, modular, multimodal biosignal acquisition architecture (M3BA) based on a high performance analog front end optimized for bio-potential acquisition, a microcontroller and our open fNIRS technology.

Main results: The designed M3BA modules are very small configurable high precision and low noise (EEG inp. ref. noise @ 500 SPS 1.39 µV, fNIRS noise equivalent power NEP$_{750\ nm}$=5.92 pW$_{pp}$, NEP$_{850\ nm}$=4.77 pW$_{pp}$) modules with full input linearity, bluetooth, 3D accelerometer and low power consumption. That allow flexible bio-potential reference setups and use in Wireless Body Area/Sensor Network (WBAN/WBSN) scenarios.

Significance: The M3BA architecture can facilitate custom designs by researchers that need to build their own hybrid multimodal biosignal acquisition hardware for mobile applications in scenarios that will increasingly include multimodal wearable sensors and telemedicine applications in the future.

The invention claimed is:

1. A biosignal acquisition device for the acquisition of optical and electrical biosignals comprising at least one EEG sensor for receiving electrical biosignals and at least one fNIRS sensor for receiving optical biosignals, wherein the optical and electrical biosignals are both received by an analog front end device for biosignals, with an opto-electric converter for converting the optical biosignals into electrical signals,
 wherein the signal acquisition is part of a closed-loop system involving optical and electrical sensors and at least one optical emitter, and
 wherein the biosignal acquisition device comprises a synchronizer configured to synchronize the optical and electrical biosignals at a sampling rate of data ready signals set by an internal oscillator, wherein synchronizing the optical and electrical biosignals provides a trigger for switching the at least one optical emitter and the at least one fNIRS sensor for the optical biosignals, thereby synchronizing the acquisition of the optical and electrical biosignals.

2. The biosignal acquisition device according to claim 1, wherein the analog front end device transmits data to a microcontroller for further processing.

3. The biosignal acquisition device according to claim 1, further comprising at least one differential biopotential sensor at least one ECG sensor, at least one EMG sensor, at least one EOG sensor, and/or at least one pulsoxymeter sensor, the data of these optical and electrical sensors being transmitted to the analog front end device.

4. The biosignal acquisition device according to claim 1, wherein the analog front end device and/or a microcontroller control an emitter of optical signals, in particular an NIR emitter.

5. The biosignal acquisition device according to claim 1, wherein a circuit line layout is designed to minimize interference.

6. The biosignal acquisition device according to claim 5, wherein the circuit line layout is designed to minimize interference by:
 integrating the components on a single multilayer circuit board so that the circuit layout and the potential surface are used as shielding means to minimize noise and/or cross-talk; and/or
 star ground design; and/or
 a multilayer design, wherein the lines are positioned between supply and ground for shielding and splitting of analog and digital domains.

7. The biosignal acquisition device according to claim 1, wherein the analog front end device comprises a processor for bipolar biosignals.

8. The biosignal acquisition device according to claim 7, wherein the bipolar biosignals are ECG or EEG biosignals.

9. The biosignal acquisition device according to claim 1, further comprising a switch for at least one measurement input of the biosignals between two possibilities for a reference.

10. The biosignal acquisition device according to claim 9, wherein the switch is a switch between a common reference with other measured biosignals or a dedicated reference separated from the other measured biosignals.

11. The biosignal acquisition device according to claim 1, further comprising at least one motion sensor.

12. The biosignal acquisition device according to claim 11, wherein the motion sensor is an accelerometer and/or a gyroscope.

13. A system of a plurality of biosignal acquisition devices according to claim 1.

14. The system according to claim 13, wherein the biosignal acquisition devices are part of modules which are identical to each other.

15. The system according to claim 13, wherein the biosignal acquisition devices as modules are coupled among each other.

16. The system according to claim 13, wherein each biosignal acquisition device comprises a common ground.

17. The system according to claim 16, wherein each biosignal acquisition device comprises a common ground through a physical interface.

18. A biosignal acquisition method for the concurrent acquisition of optical and electrical biosignals, wherein the optical and electrical biosignals are both received by a biosignal acquisition device comprising at least one EEG sensor for receiving electrical biosignals, at least one fNIRS sensor for receiving optical biosignals, and an analog front end device for biosignals, and the optical biosignals are converted by an opto-electric coupler into electrical signals,
 wherein the signal acquisition is part of a closed-loop system involving optical and electrical sensors and at least one optical emitter, and
 wherein the biosignal acquisition device comprises a synchronizer configured to synchronize the optical and electrical biosignals at a sampling rate of data ready signals set by an internal oscillator, wherein synchronizing the optical and electrical biosignals provides a trigger for switching the at least one optical emitter and the at least one fNIRS sensor for the optical biosignals, thereby synchronizing the acquisition of the optical and electrical biosignals.

\* \* \* \* \*